United States Patent
Takemura et al.

(10) Patent No.: US 12,190,507 B2
(45) Date of Patent: Jan. 7, 2025

(54) IMAGE PROCESSING DEVICE AND STORAGE MEDIUM

(71) Applicant: Konica Minolta, Inc., Tokyo (JP)

(72) Inventors: Tomoaki Takemura, Osaka (JP); Hisashi Wada, Tokyo (JP); Hidekazu Takahashi, Toyonaka (JP)

(73) Assignee: KONICA MINOLTA, INC., Tokyo (JP)

( * ) Notice: Subject to any disclaimer, the term of this patent is extended or adjusted under 35 U.S.C. 154(b) by 357 days.

(21) Appl. No.: 17/591,680

(22) Filed: Feb. 3, 2022

(65) Prior Publication Data
US 2022/0254013 A1  Aug. 11, 2022

(30) Foreign Application Priority Data
Feb. 5, 2021 (JP) .................. 2021-017378

(51) Int. Cl.
*G06T 7/00* (2017.01)
*A61B 6/50* (2024.01)

(52) U.S. Cl.
CPC ............ *G06T 7/0012* (2013.01); *A61B 6/502* (2013.01); *G06T 2207/30068* (2013.01)

(58) Field of Classification Search
CPC ......... G06T 7/0012; G06T 2207/30068; A61B 6/502
See application file for complete search history.

(56) References Cited

U.S. PATENT DOCUMENTS

2019/0269460 A1* 9/2019 Kim .................. A61B 17/3403
2021/0035285 A1* 2/2021 Sainz de Cea ....... G06T 7/0012

FOREIGN PATENT DOCUMENTS

JP  2015231438 A  * 12/2015
WO  2010110058 A1  9/2010

OTHER PUBLICATIONS

Fujifilm Medical Co., Ltd., "High-speed display of high-definition digital mammography images, Support a series of workflows from image display to report creation with one unit, Diagnostic imaging workstation dedicated to mammography, New release of "Amulet Bellus"", Mar. 7, 2013, 8 pages.
JPO Notice of Reasons for Refusal for corresponding JP Application No. 2021-017378; Dated Aug. 6, 2024; 6 pages.

* cited by examiner

*Primary Examiner* — Khai M Nguyen
(74) *Attorney, Agent, or Firm* — CANTOR COLBURN LLP

(57) ABSTRACT

Provided is an image processing device that includes a hardware processor. The hardware processor calculates a feature amount relevant to a breast shape from a mammography image. The hardware processor selects a schema image corresponding to the breast shape of the mammography image from a plurality of types of predetermined schema images based on the feature amount relevant to the breast shape calculated by the hardware processor.

4 Claims, 4 Drawing Sheets

FIG.6
| CLASSIFICATION | MLO | CC |
|---|---|---|
| CLASSIFICATION 1 |  |  |
| CLASSIFICATION 2 |  |  |
| CLASSIFICATION 3 |  |  |
| CLASSIFICATION 4 |  | 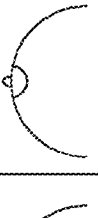 |
| CLASSIFICATION 5 |  |  |
| CLASSIFICATION 6 |  |  |

IMAGE PROCESSING DEVICE AND STORAGE MEDIUM

CROSS-REFERENCE TO RELATED APPLICATIONS

The present invention claims priority under 35 U.S.C. § 119 to Japanese Patent Application No. 2021-017378 filed on Feb. 5, 2021 the entire contents of which being incorporated herein by reference.

BACKGROUND

Technological Field

The present invention relates to an image processing device and a storage medium.

Description of the Related Art

It has been conventionally practiced to acquire mammography images of MLO (Medio-Lateral Oblique) and CC (Cranio-Caudal) by mammography and interpret the mammography images by a specialist. The position of a lesion detected by the interpretation is marked on a schema image by the interpreter while comparing the mammography image with a standard breast shape schema image (schematic breast diagram) and attached to the interpretation report.

FUJIFILM Medical Co., Ltd., "High-speed display of high-definition digital mammography images, Support a series of workflows from image display to report creation with one unit, Diagnostic imaging workstation dedicated to mammography, New release of "AMULET Bellus"", [online], [Searched on Jan. 18, 2021], Internet <URL: http://fms.fujifilm.co.jp/news/articlenr_130307.html> describes a technique for recognizing a breast shape from a mammography image instead of a standard schema image and creating a schema image showing each breast shape.

SUMMARY

However, since the breast shape varies greatly from person to person, when a standard schema image is used, the breast shape in the mammography image and the breast shape in the standard schema image may be significantly different. In this case, it takes time and effort to grasp to which position the lesion position on the mammography image corresponds on the schema image.

On the other hand, in the technique in the above-described document of FUJIFILM Medical Co., Ltd., it is possible to obtain a schema image showing the breast shape of each mammography image. However, since the mammography image is captured by compressing the breast, the breast shape on the mammography image is different for each imaging even in the case of the same subject's breast. For this reason, even for the same subject's breast, the schema image is different for each imaging (for each mammography image). For example, inconveniences such as difficulty in matching the lesion positions detected in the past on the schema image generated based on the mammography image captured this time may occur, which is not preferable.

An object of the present invention is to make it possible to provide a schema image corresponding to the breast shape of a mammography image without providing a different schema image for each capturing of a mammography image for the same subject.

To achieve at least one of the abovementioned objects, an image processing device reflecting one aspect of the present invention includes:
  a hardware processor,
  wherein the hardware processor calculates a feature amount relevant to a breast shape from a mammography image, and
  the hardware processor selects a schema image corresponding to the breast shape of the mammography image from a plurality of types of predetermined schema images based on the feature amount relevant to the breast shape calculated by the hardware processor.

To achieve at least one of the abovementioned objects, a storage medium reflecting another aspect of the present invention stores a computer readable program causing a computer to execute:
  calculating a feature amount relevant to a breast shape from a mammography image; and
  selecting a schema image corresponding to the breast shape of the mammography image from a plurality of types of predetermined schema images based on the calculated feature amount relevant to the breast shape.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 6 is a diagram showing examples of schema images of MLO images and CC images corresponding to respective Classifications 1 to 6.

DETAILED DESCRIPTION OF THE EMBODIMENTS

Hereinafter, embodiments of the present invention will be described with reference to the diagrams. However, the embodiments described below are provided with various technically preferable limitations for carrying out the present invention. Therefore, the technical scope of the present invention is not limited to the following embodiments and illustrated examples.

(Configuration of a Medical Image System 100)

First, the configuration of the medical image system 100 including an image processing device 2 that is an embodiment of an image processing device of the present invention will be described.

Figure 1:
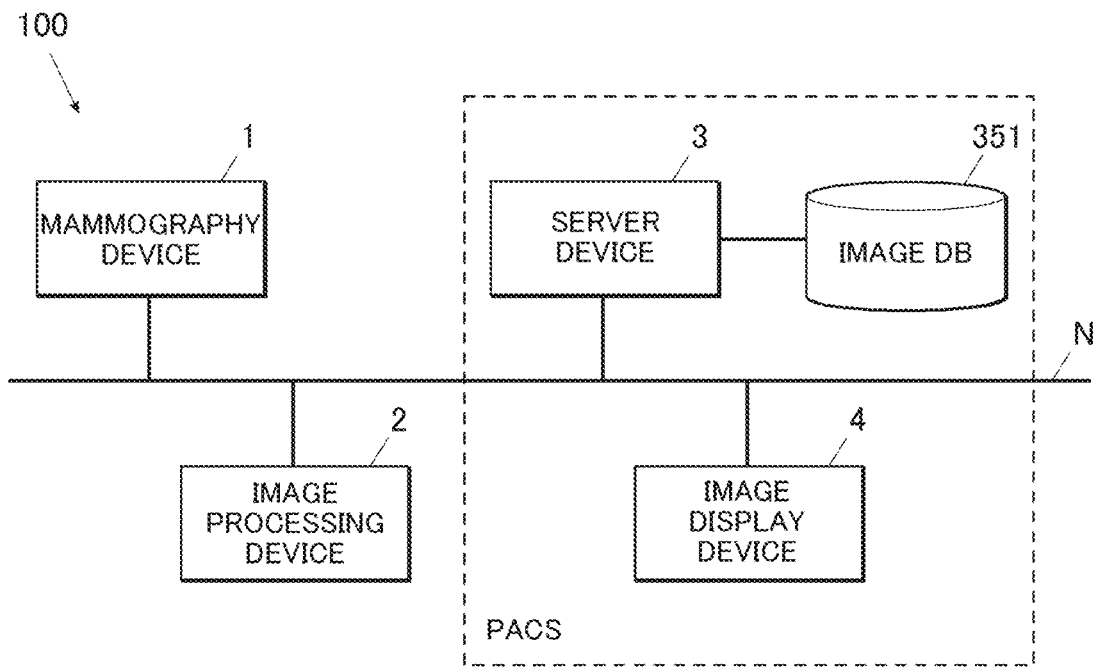
FIG. 1 is a diagram showing an overall configuration example of a medical imaging system according to the present embodiment.

FIG. 1 shows a system configuration of the medical image system 100 according to the present embodiment.

As shown in FIG. 1, the medical image system 100 includes a mammography device 1, the image processing device 2, a server device 3, and an image display device 4 (output unit). These devices 1 to 4 are connected to each other through a communication network N constructed in a medical facility, such as a local area network (LAN), so as to be able to transmit and receive data to and from each other. The number of devices is not particularly limited.

The mammography device 1 is an X-ray imaging device that images a breast with X-rays to generate a digital mammography image (mammography image data) and transmits the digital mammography image (mammography image data) to the image processing device 2 and the server device 3.

The mammography device 1 can receive various kinds of information attached to each generated mammography image, for example, patient information or examination information from the outside, and can also automatically generate the information. The patient information includes patient identification information (for example, a patient ID) for identifying a patient (subject) and information of patient name, gender, date of birth, and the like. The examination information includes examination identification information (for example, an examination ID) for identifying an examination and information of examination date and time, examination conditions (examination part, laterality (left, right), direction (for example, cranio-caudal (CC), and mediolateral oblique (MLO))), modality type, and the like. In the present embodiment, it is assumed that the examination ID is managed by assigning the same examination ID to a series of images (two left and right MLO images and CC images) acquired by mammography examination on the same patient. The mammography device 1 adds the patient information or the examination information, a UID (unique ID) for identifying an image, and the like to the generated mammography image as additional information, and transmits the additional information to the image processing device 2 and the server device 3 through the communication network N.

The image processing device 2 is a computer that selects a schema image corresponding to the breast shape of the mammography image generated by the mammography device 1 from a plurality of types of schema images prepared in advance, associates the selected schema image with the UID of the mammography image, and transmits the selected schema image associated with the UID of the mammography image to the server device 3.

Figure 2:
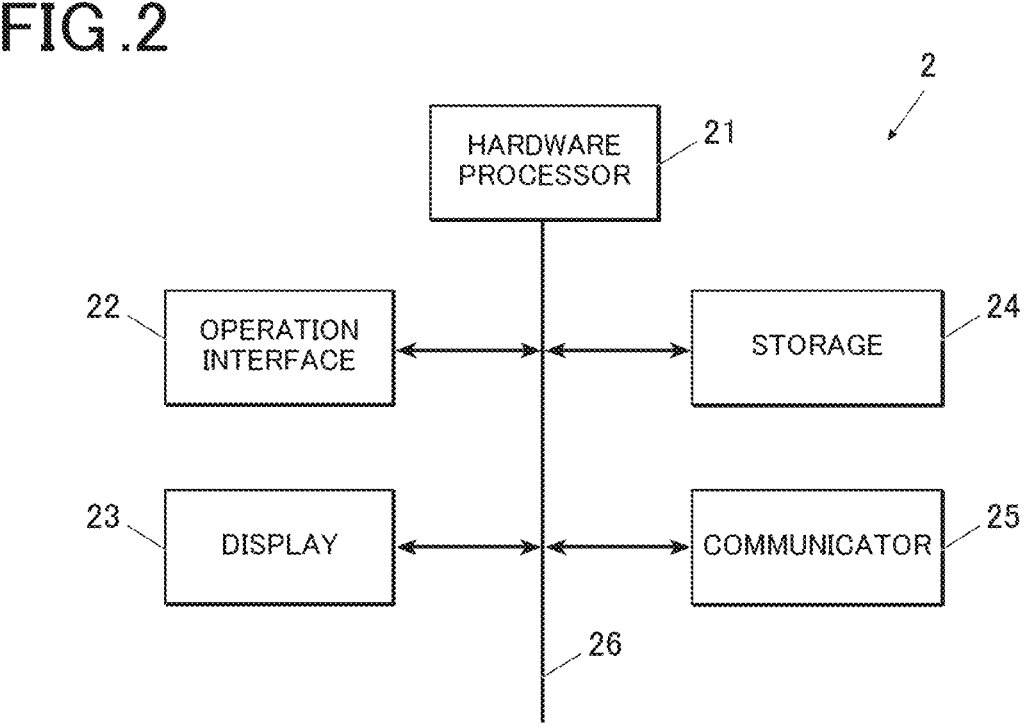
FIG. 2 is a block diagram showing the functional configuration of an image processing device in FIG. 1.

FIG. 2 shows an example of the functional configuration of the image processing device 2. As shown in FIG. 2, the image processing device 2 includes a hardware processor 21, an operation interface 22, a display 23, a storage 24, and a communicator 25, and these are connected to each other through a bus 26.

The hardware processor 21 includes a CPU (central processing unit), a RAM (random access memory), and the like. The CPU of the hardware processor 21 reads various programs such as system programs and processing programs stored in the storage 24 and loads the programs to the RAM, and executes various processes according to the loaded programs. For example, the hardware processor 21 functions as a calculation means and a selection means by executing a schema image selection process described later.

The operation interface 22 includes a keyboard with character input keys, number input keys, various function keys, and the like and a pointing device, such as a mouse, and outputs a press signal of a key pressed on the keyboard and an operation signal by the mouse to the hardware processor 21 as an input signal.

The display 23 include, for example, a monitor such as a CRT (Cathode Ray Tube) or an LCD (Liquid Crystal Display), and displays various screens according to an instruction of a display signal input from the hardware processor 21.

The storage 24 is, for example, an HDD (Hard Disk Drive) or a semiconductor non-volatile memory. As described above, various programs are stored in the storage 24.

A plurality of types of schema images (identification information and image data of schema images) having different breast shapes and classification information (Classifications 1 to 6 in the present embodiment) of a breast shape corresponding to each schema image are stored in the storage 24.

The communicator 25 is, for example, a LAN card, and transmits and receives data to and from an external device connected to the communication network N through a switching hub.

The server device 3 configures a PACS (Picture Archiving and Communication System) together with the image display device 4 that is a client. The server device 3 includes a hardware processor, an operation interface, a display, a communicator, and a storage having an image DB 351. The server device 3 stores the mammography image generated by the mammography device 1 in the image DB 351 so as to be associated with additional information (UID, patient information, or examination information) and a schema image corresponding to the mammography image, and manages the stored mammography image. According to the instruction from the image display device 4, the server device 3 causes the image display device 4 to display an examination list screen for the user to select an examination to be read, a viewer screen for reading a mammography image of the selected examination from the image DB 351 and displaying the mammography image, a report screen for displaying a schema image corresponding to the displayed mammography image and receiving the input of the interpretation report, and the like. Then, the image interpretation report input from the image display device 4 is stored in the image DB 351 so as to be associated with the examination information.

The image display device 4 displays the examination list screen, the viewer screen, the report screen, and the like transmitted from the server device 3, and displays information input from these screens or transmits the information to the server device 3. The image display device 4 functions as an output unit that outputs a schema image selected by a schema image selection process described later.

(Operation of the Medical Image System 100)

Next, the operation of the medical image system 100 will be described.

As described above, since the breast shape varies greatly from person to person, if a standard schema image is used for recording a lesion in a mammography image as in the relevant art, the breast shape in the mammography image and the breast shape in the standard schema image may be significantly different. In this case, it takes time and effort for the user to grasp to which position the lesion position on the mammography image corresponds on the schema image.

On the other hand, it is also performed to recognize the breast shape of each mammography image and create a schema image. However, since the mammography image is captured by compressing the breast, the breast shape on the mammography image is different for each imaging even in the case of the same subject's breast. For this reason, even in the case of the same subject's breast, the schema image becomes different for each imaging (for each mammography image).

Therefore, in the present embodiment, the medical image system 100 includes the image processing device 2, and the image processing device 2 determines into which of a plurality of predetermined types the breast shape of the mammography image generated by the mammography device 1 is to be classified based on the characteristics of the breast shape, and selects a schema image corresponding to the determination result, as a schema image corresponding to the mammography image, from a plurality of types of schema images having different breast shapes.

Figure 3:
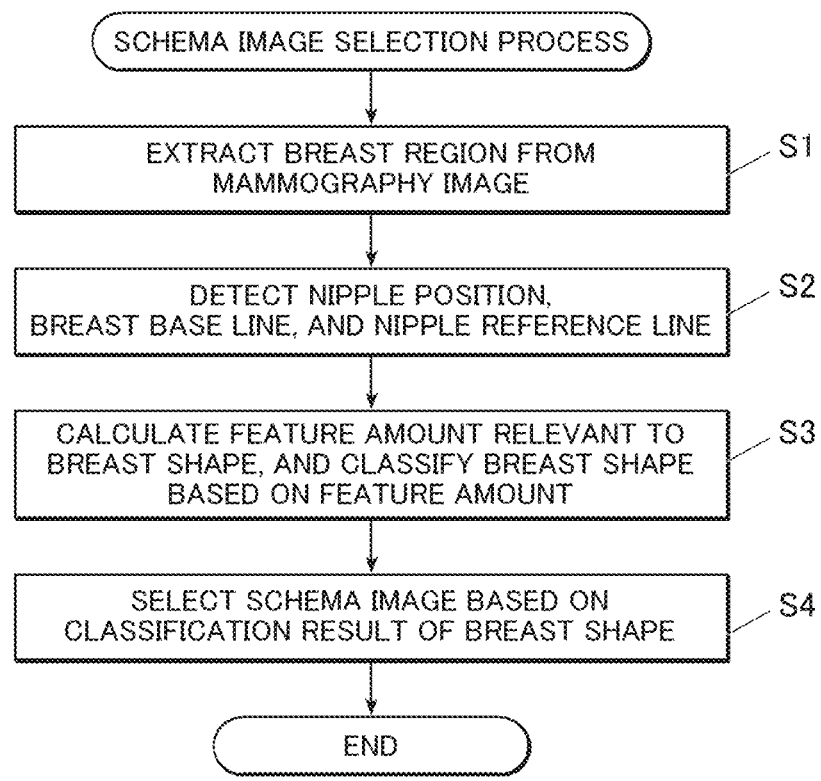
FIG. 3 is a flowchart showing a schema image selection process executed by a hardware processor in FIG. 2.

FIG. 3 is a flowchart showing the flow of the schema image selection process executed by the hardware processor 21 of the image processing device 2. The schema image selection process is executed by cooperation of the CPU of the hardware processor 21 and a program stored in the storage 24 by using the received mammography image as a processing target when the mammography image from the mammography device 1 is received by the communicator 25.

First, the hardware processor 21 extracts a breast region from the received mammography image (step S1).

Any known method may be used to extract the breast region from the mammography image. For example, it is possible to use a method in which a histogram analysis of a mammography image is performed to obtain a brightness value of a skin line, which is a boundary between a breast region and a non-breast region, and the breast region is extracted based on the skin line obtained by searching for a pixel having the brightness value from the chest wall side to the nipple side. Alternatively, for example, a region where the brightness value (X-ray intensity) changes may be extracted from the mammography image by using a Sobel filter, only a region where the degree of change in the brightness value is equal to or greater than a threshold value may be extracted by binarization, and contour extraction may be performed to extract the breast region.

Then, the hardware processor 21 detects a nipple position, a breast base line, and a nipple reference line from the mammography image (step S2).

Figure 4:
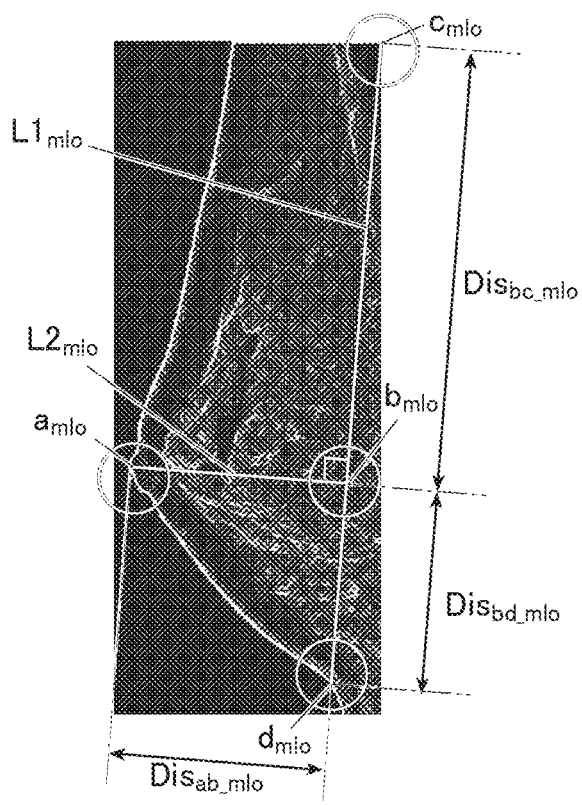
FIG. 4 is a diagram for explaining a method for calculating a feature amount relevant to the breast shape in an MLO image.
Figure 5:
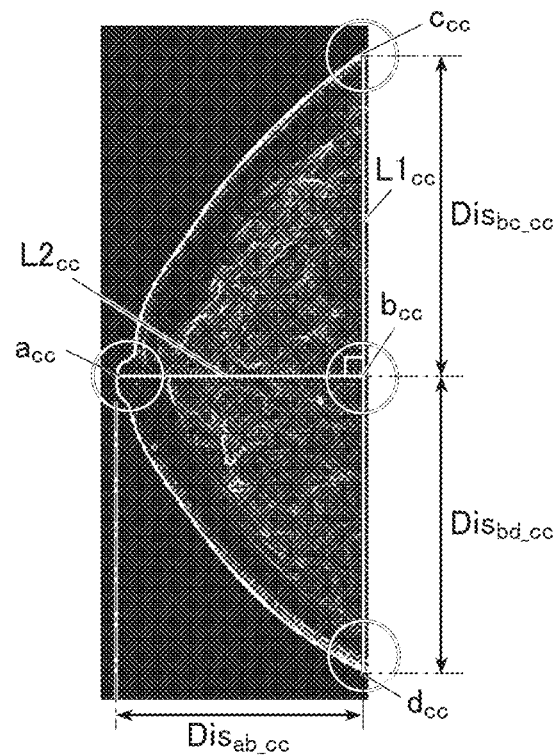
FIG. 5 is a diagram for explaining a method for calculating a feature amount relevant to the breast shape in a CC image.

FIG. 4 is a diagram showing a nipple position $a_{mlo}$, a breast base line $L1_{mlo}$, and a nipple reference line $L2_{mlo}$ in a mammography image (referred to as an MLO image) in the MLO direction. FIG. 5 is a diagram showing a nipple position ace, a breast base line $L1_{cc}$, and a nipple reference line $L2_{cc}$ in a mammography image (referred to as a CC image) in the CC direction. The subscript mlo is attached to the parameters in the MLO image, and the subscript cc is attached to the parameters in the CC image.

The nipple position $a_{mlo}$ ($a_{cc}$) can be detected by using, for example, known methods described in JP 2015-104464 A, JP 2015-104465 A, and the like.

The breast base line $L1_{mlo}$ ($L1_{cc}$) is a line showing the outer edge of the basal part of the breast in the mammography image, and the line connecting the upper end of the breast curio ($c_{cc}$) and the lower end of the breast $d_{mlo}$ ($d_{cc}$) to each other is detected as the breast base line $L1_{mlo}$ ($L1_{cc}$). In the MLO image, as shown in FIG. 4, the upper end of the breast region on the chest wall side in the mammography image can be defined as the upper end of the breast $c_{mlo}$. If the upper end of the breast $c_{mlo}$ ($c_{cc}$) or the lower end of the breast $d_{mlo}$ ($d_{cc}$) cannot be detected, the chest wall line may be detected and set as the breast base line $L1_{mlo}$ (L1cc), and the image edge on the chest wall side in the breast region of the mammography image may be set as the breast base line $L1_{mlo}$ ($L1_{cc}$).

The nipple reference line $L2_{mlo}$ ($L2_{cc}$) can be detected by drawing a perpendicular line from the nipple position $a_{mlo}$ ($a_{cc}$) to the breast base line $L1_{mlo}$ ($L1_{cc}$).

Then, the hardware processor 21 calculates a feature amount relevant to the breast shape from the mammography image, and classifies the breast shape of the breast included in the mammography image into one of a plurality of types based on the calculated feature amount (step S3).

The breast shape varies greatly from person to person, but can be classified into a plurality of types according to the characteristics of the breast shape, for example. The method of classifying the breast shape is not particularly limited. In the present embodiment, an example of classifying the breast shape into the following six types based on the volume (bulge) of the breast and the position of the nipple will be described.

Classification 1: Small volume and flat.

Classification 2: Larger volume than that of Classification 1, but slightly smaller.

Classification 3: The breast hangs diagonally downward.

Classification 4: Larger volume than that of Classification 2 and plump and swelling.

Classification 5: There is no height at the top of the nipple, and the nipple position is slightly lowered.

Classification 6: Even larger than that of Classification 4, and protruding upward.

First, an example of classifying the breast shape of the MLO image by using, for example, $p_{mlo}$, which is a feature amount relevant to the volume of the breast included in the MLO image, and $q_{mlo}$, which is a feature amount relevant to the nipple position, will be described.

$p_{mlo}$ is the ratio of the length of the perpendicular line (nipple reference line $L2_{mlo}$) drawn from the nipple position $a_{mlo}$ to the breast base line Limbo to the length of the breast base line Limbo in the MLO image. In the case of the example shown in FIG. 4, $p_{mlo}$ can be calculated by the following Equation (1). $p_{mlo}$ is a large value when the volume of the breast is large, and is a small value when the volume of the breast is small.

[Equation 1]

$$p_{mlo} = \frac{Dis_{ab\_mlo}}{Dis_{bc\_mlo} + Dis_{bd\_mlo}} \quad (1)$$

$q_{mlo}$ is the ratio of the length between the lower end $d_{mlo}$ of the breast base line Limbo and the intersection $b_{mlo}$ between the perpendicular line (nipple reference line $L2_{mlo}$), which is drawn from the nipple position $a_{mlo}$ to the breast base line Limbo, and the breast base line Limbo to the length of the breast base line Limbo in the MLO image. In the case of the example shown in FIG. 4, $q_{mlo}$ can be calculated by the following Equation (2). $q_{mlo}$ is a large value when the nipple position $a_{mlo}$ is above the upper end, and is a small value when the nipple position $a_{mlo}$ is above the lower end.

[Equation 2]

$$q_{mlo} = \frac{Dis_{bd\_mlo}}{Dis_{bc\_mlo} + Dis_{bd\_mlo}} \quad (2)$$

$Dis_{ab\_mlo}$ is the length of the line segment $a_{mlo}b_{mlo}$ (the line segment length of the vertical line (nipple reference line L2) from $a_{mlo}$ to the breast base line $L1_{mlo}$). $Dis_{bc\_mlo}$ is the length of the line segment $b_{mlo}c_{mlo}$. $Dis_{bd\_mlo}$ is the length of the line segment $b_{mlo}d_{mlo}$.

The hardware processor 21 calculates the values of $p_{mlo}$ and $q_{mlo}$ from the MLO image, and compares the values of $p_{mlo}$ and $q_{mlo}$ with predetermined threshold values shown in Table 1 below to classify the breast shape of the MLO image into one of Classifications 1 to 6.

TABLE 1

| Classification | $p_{mlo} = \frac{Dis_{ab\_mlo}}{Dis_{bc\_mlo} + Dis_{bd\_mlo}}$ | $q_{mlo} = \frac{Dis_{bd\_mlo}}{Dis_{bc\_mlo} + Dis_{bd\_mlo}}$ |
|---|---|---|
| Classification 1 | $0 \leq p_{mlo} < 0.3$ | $0.33 \leq q_{mlo}$ |
| Classification 2 | $0.3 \leq p_{mlo} < 0.5$ | $0.33 \leq q_{mlo}$ |
| Classification 3 | $0.5 \leq p_{mlo}$ | $q_{mlo} < 0.33$ |
| Classification 4 | $0.5 \leq p_{mlo} < 0.7$ | $0.33 \leq q_{mlo}$ |
| Classification 5 | $0 \leq p_{mlo} < 0.5$ | $q_{mlo} < 0.33$ |
| Classification 6 | $0.7 \leq p_{mlo}$ | $0.33 \leq q_{mlo}$ |

The ranges of $p_{mlo}$ and $q_{mlo}$ in each of Classifications 1 to 6 shown in Table 1 are examples, and are not limited to those shown in Table 1.

Next, an example of classifying the breast shape of the CC image will be described.

Even when the breast shapes are different as in Classifications 1 to 6, the breast shape of the CC image is a similar semicircular shape due to compression at the time of imaging. For this reason, it is difficult to classify the breast shape of the CC image into Classifications 1 to 6. In this example, a method of classifying the breast shape of the CC image into either Classification 1 or other Classifications 2 to 6 based on the feature amount pc, will be described.

$p_{cc}$ is the ratio of the length of the perpendicular line (nipple reference line L2cc) drawn from the nipple position $a_{cc}$ to the breast base line $L1_{cc}$ to the length of the breast base line $L1_{cc}$ in the CC image. In the case of the example shown in FIG. 5, $p_{cc}$ can be calculated by the following Equation (3). $p_{cc}$ is a large value when the volume of the breast is large, and is a small value when the volume of the breast is small.

[Equation 3]

$$p_{cc} = \frac{Dis_{ab\_cc}}{Dis_{bc\_cc} + Dis_{bd\_cc}} \quad (3)$$

$Dis_{ab\_cc}$ is the length of the line segment $a_{cc}b_{cc}$ (the line segment length of the vertical line (nipple reference line L2$_{cc}$) from $a_{cc}$ to the breast base line $L1_{cc}$). $Dis_{bc\_cc}$ is the length of the line segment $b_{cc}c_{cc}$. $Dis_{bd\_cc}$ is the length of the line segment $b_{cc}d_{cc}$.

The hardware processor 21 calculates $p_{cc}$ from the CC image, and compares this value with a predetermined threshold value shown in Table 2 below to determine whether the breast shape of the CC image is classified into Classification 1 or Classifications 2 to 6.

TABLE 2

| Classification | $p_{cc} = \frac{Dis_{ab\_cc}}{Dis_{bc\_cc} + Dis_{bd\_cc}}$ |
|---|---|
| Classification 1 | $p_{cc} < 0.5$ |
| Classification 2 | $0.5 \leq p_{cc}$ |
| Classification 3 | $0.5 \leq p_{cc}$ |
| Classification 4 | $0.5 \leq p_{cc}$ |
| Classification 5 | $0.5 \leq p_{cc}$ |
| Classification 6 | $0.5 \leq p_{cc}$ |

Then, the hardware processor 21 selects a schema image corresponding to the breast shape of the mammography image from a plurality of types of schema images based on the classification result of the breast shape (step S4), and ends the schema image selection process.

FIG. 6 is a diagram showing examples of schema images of MLO images and CC images corresponding to the respective Classifications 1 to 6. Since the breast shapes of Classification 2, Classification 4, and Classification 5 are similar in the MLO image, the same schema image is selected in the present embodiment. However, different schema images may be prepared for each classification, and a different schema image may be selected for each classification. In the present embodiment, the same schema image is selected for Classifications 2 to 6 of the CC image. However, different schema images may be prepared for each classification, and a different schema image may be selected for each classification.

In this manner, the feature amount of the breast shape of the mammography image is calculated, and the schema image corresponding to the breast shape of the mammography image is selected from a plurality of types of schema images based on the calculated feature amount. Therefore, it is possible to provide a schema image corresponding to the breast shape of the mammography image without providing a different schema image for each capturing of a mammography image.

When the schema image selection process ends, the hardware processor 21 associates the UID of the received mammography image with the selected schema image and transmits the schema image associated with the UID to the server device 3 through the communicator 25.

When the server device 3 receives the UID and the schema image transmitted from the image processing device 2, the received schema image is stored in the image DB 351 so as to be associated with the UID.

When an examination is selected from the examination list screen displayed on the image display device 4 and an instruction to display the viewer screen of the selected examination is given, the server device 3 reads the mammography image of the selected examination from the image DB 351 and transmits the read mammography image to the image display device 4 so that the viewer screen on which the mammography image is displayed is displayed on the image display device 4. When an instruction to display the report screen of the selected examination is given, the server device 3 reads the schema image corresponding to the mammography image of the selected examination from the image DB 351 and transmits the read schema image to the image display device 4 so that the report screen on which the schema image is displayed is displayed on the image display device 4.

On the image display device 4, the interpreter interprets the mammography image displayed on the viewer screen and when a lesion is detected, marks the lesion position on the schema image displayed on the report screen. At this time, since the schema image corresponding to the breast shape of the mammography image is selected, the interpreter can greatly reduce the time and effort required to associate the breast shape in the mammography image with the breast shape in the schema image or the time and effort required to grasp to which position the lesion position on the mammography image corresponds on the schema image. In addition, since a different schema image is not provided for each capturing of the mammography image for the same subject, the lesion position detected in the past and the lesion position detected from the mammography image captured this time can be easily compared with each other on the schema image.

While the embodiment of the present invention has been described above, the description in each of the above embodiments is a preferable example of the present invention, and the present invention is not limited thereto.

For example, in the above embodiment, the image processing device 2 has been described as a device separate from the server device 3, but the server device 3 may be configured to have the functions of the image processing device 2. For example, when the server device 3 receives a mammography image from the mammography device 1, the hardware processor of the server device 3 may execute the schema image selection process shown in FIG. 3 on the received mammography image, and the selected schema image may be stored in the image DB 351 so as to be associated with the UID. Alternatively, the image display device 4 may be configured to have the functions of the image processing device 2. For example, when an examination is selected from the examination list screen displayed on the image display device 4, the hardware processor of the image display device 4 may read the mammography image of the selected examination from the image DB 351 and execute the schema image selection process shown in FIG. 3 on the read mammography image. Then, the selected schema image may be displayed (output) on the report screen.

In the above embodiment, after selecting the schema image, the hardware processor 21 associates the UID of the received mammography image with the selected schema image and transmits the schema image associated with the UID to the server device 3 through the communicator 25. However, a plurality of types of schema images may be stored in the server device 3 so as to be associated with the identification information of the schema images and after selecting a schema image, the hardware processor 21 may associate the UID of the received mammography image with the identification information of the selected schema image and transmit the schema image associated with the UID to the server device 3 through the communicator 25. Then, in the server device 3, the identification information of the received schema image may be stored in the image DB 351 so as to be associated with the UID. As the identification information of the schema image, the classification name (Classifications 1 to 6) of the mammography image corresponding to the schema image may be used.

In the above embodiment, the case where $p_{mlo}$, which is a feature amount relevant to the volume of the breast, and $g_{mlo}$, which is a feature amount relevant to the nipple position, are used as feature amounts relevant to the breast shape of the mammography image has been described as an example. However, the present invention is not limited thereto, and other feature amounts may be used.

In the above description, an example is disclosed in which a hard disk, a semiconductor non-volatile memory, or the like is used as a computer-readable medium for a program according to the present invention, but the present invention is not limited to this example. As other computer-readable media, a portable recording medium, such as a CD-ROM, can be applied. A carrier wave is also applied as a medium for providing data of the program according to the present invention through a communication line.

The detailed configuration and detailed operation of each device included in the medical image system can also be appropriately changed without departing from the spirit of the present invention.

What is claimed is:

1. An image processing device, comprising:
a hardware processor,
wherein the hardware processor calculates a feature amount relevant to a breast shape from a mammography image, and
the hardware processor selects a schema image corresponding to the breast shape of the mammography image from a plurality of types of predetermined schema images based on the feature amount relevant to the breast shape calculated by the hardware processor:
wherein the feature amount relevant to the breast shape is a feature amount relevant to a volume of a breast included in the mammography image or a feature amount relevant to a position of a nipple;
wherein the feature amount relevant to the volume of the breast is a ratio of a length of a perpendicular line drawn from the nipple to a breast base line in the mammography image to a length of the breast base line.

2. The image processing device according to claim 1, wherein the feature amount relevant to the position of the nipple is a ratio of a length between a lower end of the breast base line and an intersection between the breast base line and a perpendicular line, which is drawn from the nipple to the breast base line, to a length of the breast base line in the mammography image.

3. The image processing device according to claim 1, further comprising:
an output unit that outputs the schema image selected by the hardware processor.

4. A non-transitory recording medium storing a computer readable program causing a computer to execute:
calculating a feature amount relevant to a breast shape from a mammography image; and
selecting a schema image corresponding to the breast shape of the mammography image from a plurality of types of predetermined schema images based on the calculated feature amount relevant to the breast shape:
wherein the feature amount relevant to the breast shape is a feature amount relevant to a volume of a breast included in the mammography image or a feature amount relevant to a position of a nipple;
wherein the feature amount relevant to the volume of the breast is a ratio of a length of a perpendicular line drawn from the nipple to a breast base line in the mammography image to a length of the breast base line.

* * * * *